United States Patent
Kato et al.

(10) Patent No.: US 9,297,729 B2
(45) Date of Patent: Mar. 29, 2016

(54) METHOD FOR EVALUATING HIT FEELING

(75) Inventors: Masatoshi Kato, Kobe (JP); Naoyoshi Ueda, Kobe (JP); Masahiko Ueda, Kobe (JP); Takeshi Asakura, Kobe (JP)

(73) Assignee: DUNLOP SPORTS CO., LTD., Kobe-shi (JP)

( * ) Notice: Subject to any disclaimer, the term of this patent is extended or adjusted under 35 U.S.C. 154(b) by 449 days.

(21) Appl. No.: 13/450,089

(22) Filed: Apr. 18, 2012

(65) Prior Publication Data

US 2012/0266652 A1 Oct. 25, 2012

(30) Foreign Application Priority Data

Apr. 19, 2011 (JP) .................. 2011-092569
Dec. 5, 2011 (JP) .................. 2011-265484

(51) Int. Cl.
*G01N 3/30* (2006.01)
*G01P 15/00* (2006.01)

(52) U.S. Cl.
CPC .......... *G01N 3/30* (2013.01); *G01N 2203/0676* (2013.01); *G01P 15/00* (2013.01)

(58) Field of Classification Search
CPC A53B 2220/00; A63B 2220/40; G01P 15/00; G01P 2015/00
USPC ......... 473/246, 244, 288, 409, 342, 870, 190; 73/12.04
See application file for complete search history.

(56) References Cited

U.S. PATENT DOCUMENTS

| | | | | |
|---|---|---|---|---|
| 3,717,857 A | * | 2/1973 | Evans | 340/870.13 |
| 5,351,952 A | * | 10/1994 | Hackman | A63B 69/3632 473/233 |
| 5,441,256 A | * | 8/1995 | Hackman | A63B 53/00 473/233 |
| 6,441,745 B1 | * | 8/2002 | Gates | A63B 69/3632 340/669 |
| 6,532,818 B2 | * | 3/2003 | Blankenship | A63B 60/42 702/43 |
| 7,870,790 B2 | * | 1/2011 | Sato et al. | 73/579 |
| 8,075,417 B2 | * | 12/2011 | Thomas et al. | 473/246 |
| 8,376,873 B2 | * | 2/2013 | Golden et al. | 473/244 |
| 8,550,939 B2 | * | 10/2013 | Ueda et al. | 473/409 |
| 8,672,779 B1 | * | 3/2014 | Sakyo | A63B 24/0006 473/223 |
| 8,715,096 B2 | * | 5/2014 | Cherbini | G09B 19/0038 473/131 |
| 2002/0077189 A1 | * | 6/2002 | Tuer et al. | 473/151 |
| 2008/0115582 A1 | | 5/2008 | Sato et al. | |
| 2014/0200094 A1 | * | 7/2014 | Parke | A63F 13/00 473/223 |

FOREIGN PATENT DOCUMENTS

JP 2002-286565 A 10/2002

* cited by examiner

*Primary Examiner* — Lisa Caputo
*Assistant Examiner* — Tran M Tran
(74) *Attorney, Agent, or Firm* — Birch, Stewart, Kolasch & Birch, LLP

(57) ABSTRACT

An evaluation method for hit feeling of a sport implement according to the present invention includes an acceleration measurement step for measuring acceleration of a sport hitting tool 4 and a data analysis step for analyzing data obtained in the measurement. In the data analysis step, an amount of change in acceleration in a first cycle of vibration after hitting is calculated. The evaluation method evaluates hit feeling to be felt by a person, using the amount of change in the acceleration. Preferably, in the data analysis step, an amount of change in acceleration in the first cycle of predetermined time is calculated. The predetermined time is within 1.5 msec from the time of hitting. Preferably, the sport hitting tool 4 has the hitting section detachably attached to a shaft section.

19 Claims, 18 Drawing Sheets

METHOD FOR EVALUATING HIT FEELING

This application involves a claim for benefits based on Japanese Patent Application No. 2011-92569 filed on Apr. 19, 2011 and Japanese Patent Application No. 2011-265484 filed on Dec. 5, 2011, which are incorporated herein in their entirety by reference.

BACKGROUND OF THE INVENTION

1. Field of the Invention

The present invention relates to a method for evaluating hit feeling in sport implements.

2. Description of the Related Art

In sports, a number of sport hitting tools such as a golf club, a tennis racket, a badminton racket, a table tennis racket, a baseball bat and the like are used. Balls or shuttles to be hit with a sport hitting tool are used. There exists a hit feeling that a user has when he or she hits a ball or shuttle (hereinafter referred to as a ball and the like) with the sport hitting tool. The hit feeling is an important factor in selecting a sport implement such as sport hitting tools and ball and the like.

In Japanese Patent Application Publication No. 2002-286565, a method for evaluating hit feeling through the use of a golf ball and a golf club is proposed. In this method, hit feeling is evaluated using magnitude of impact force when a golf ball and a golf club collide with each other. In Japanese Patent Application Publication No. 2008-125722 (US2008/0115582), vibration in a circumferential direction of a golf club shaft is calculated. A method for evaluating the hit feeling with this vibration is proposed. In the methods proposed in these publications, the hit feeling can be evaluated quantitatively. These methods can evaluate the hit feeling more objectively than conventional qualitative evaluations.

In the methods proposed in these publications, when a difference in the hit feeling is small, it is difficult to recognize the difference. In addition, even though a difference in the hit feeling is observed in the qualitative evaluation, the difference may not be adequately evaluated in the quantitative evaluation. The present invention provides a method for quantitatively evaluating a difference in hit feeling even if the difference is small.

An object of the present invention is to provide an evaluation method which has excellent accuracy of evaluation of hit feeling of sport implements.

SUMMARY OF THE INVENTION

The evaluation method for hit feeling of a sport implement according to the present invention includes an acceleration measurement step for measuring acceleration of a sport hitting tool and a data analysis step for analyzing data obtained in the measurement. In the data analysis step, an amount of change in the acceleration in a first cycle of vibration after hitting is calculated. The evaluation method evaluates the hit feeling using the amount of change in the acceleration.

Preferably, in the data analysis step, the amount of change in the acceleration in the first cycle of predetermined time is calculated. The predetermined time is within 1.5 msec from the time of hitting. Preferably, the predetermined time is equal to or longer than 0.3 msec from the time of hitting.

Preferably, the amount of change in the acceleration is calculated by using a difference between maximum acceleration and minimum acceleration in the first cycle of vibration.

Preferably, in the acceleration measurement step, a swing robot holds the sport hitting tool.

Preferably, the sport hitting tool has a holding section to be held by a person, a hitting section for hitting a ball, and a shaft section connecting the hitting section with the holding section. In the acceleration measurement step, a sensor for measuring acceleration is attached to the shaft section. The sensor is attached, having a space with respect to the hitting section.

Preferably, a ratio (L1/L) of length L of the shaft section to length L1 from a position where the sensor is attached to an end of the holding section is equal to or smaller than 0.75. More preferably, the ratio (L1/L) is equal to or smaller than 0.50. More preferably, the ratio (L1/L) is equal to or smaller than 0.25.

Preferably, the sport hitting tool has a holding section to be held by a person, a hitting section for hitting a ball, and a shaft section connecting the hitting section with the holding section. The hitting section is detachably attached to the shaft section.

Preferably, the acceleration measurement step includes a hitting section preparation step, a hitting section replacement step, and a measurement data acquisition step. In the hitting section preparation step, multiple hitting sections including one hitting section and other hitting section are prepared. In the hitting section replacement step, the one hitting section is removed from the shaft section and the other hitting section is attached to the shaft section. The removal of the one hitting section is performed after acceleration is measured with the sport hitting tool provided with the one hitting section. In the measurement data acquisition step, acceleration is measured with the sport hitting tool provided with the other hitting section.

Preferably, the sport hitting tool has a holding section to be held by a person, a hitting section for hitting a ball, and a shaft section connecting the hitting section and the holding section. The hitting section has a casing and a face for hitting the ball. The face is detachably attached to the casing.

Preferably, the acceleration measurement step includes a face preparation step, a face replacement step, and a measurement data acquisition step. In the face preparation step, multiple faces including one face and other face are prepared. In the face replacement step, the one face is removed from the casing and the other face is attached to the casing. The removal of the one face is performed after acceleration is measured with the sport hitting tool provided with the one face. In the measurement data acquisition step, acceleration is measured with the sport hitting tool provided with the other face.

Preferably, the sport hitting tool is a golf club or a golf ball. Preferably, a loft angle of the golf club is equal to or greater than 20°. More preferably, the loft angle is equal to or greater than 40°. Preferably, a loft angle of a golf club for hitting the golf ball is equal to or greater than 20°. More preferably, the loft angle is equal to or greater than 40°. Preferably, the amount of change in the acceleration is calculated by using an amount of change in acceleration Ax in an X-axis direction which is an axial direction of the shaft section.

Preferably, an amount of change of the acceleration is calculated by using two or more amounts of changes including at least an amount of change of the acceleration Ax, among the amount of change in the acceleration Ax in the X-axis direction, an amount of change in acceleration Az in a Z-axis direction which is perpendicular to the X-axis direction and parallel to a hitting direction, and an amount of change in acceleration Ay in a Y-axis direction which is perpendicular to the X-axis direction and the Z-axis direction.

With the evaluation method according to the present invention, quantitative and objective evaluation result can be obtained. Compared with the conventional quantitative evaluation method, a small difference in hit feeling can be evaluated.

DESCRIPTION OF THE PREFERRED EMBODIMENTS

The present invention will be described in detail on the basis of preferred embodiments, with reference to the drawings, as appropriate.

Figure 1:
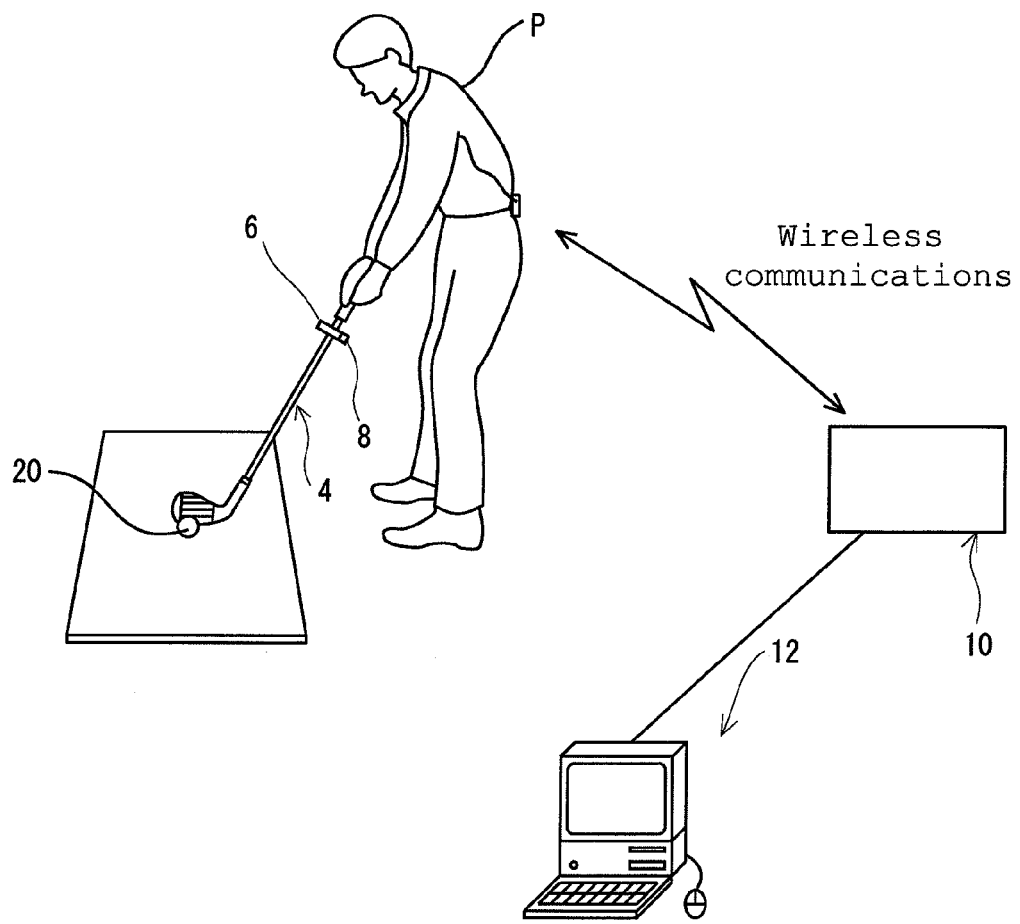
FIG. 1 is an illustration showing how an evaluation method according to one embodiment of the present invention is performed.

As shown in FIG. 1, evaluation equipment 2 is provided with a golf club 4, a fitting jig 6, a sensor 8, a controller 10, and an information processor 12.

The controller 10 is connected with the sensor 8 via wireless communications. The controller 10 is connected with the information processor 12 via wire communications. Any of the connections may be wire or wireless communications. The controller 10 transmits a measurement start signal to the sensor 8. The controller 10 receives measurement data from the sensor 8. The controller 10 transmits the measurement data to the information processor 12.

The information processor 12 has an input section, a storage section, a calculation section and an output section. Examples of the information processor 12 include a computer. In the information processor 12, the input section receives measurement data from the controller 10. The storage section stores the measurement data. The calculation section analyzes the measurement data. The calculation section determines evaluation result on the basis of the analysis result. The output section outputs the evaluation result. For example, the input section is an interface board, the storage section is a hard disk, the calculation section is a CPU, and the output section is a display. As the output section, a printer may be used together with or instead of the display.

Figure 2:
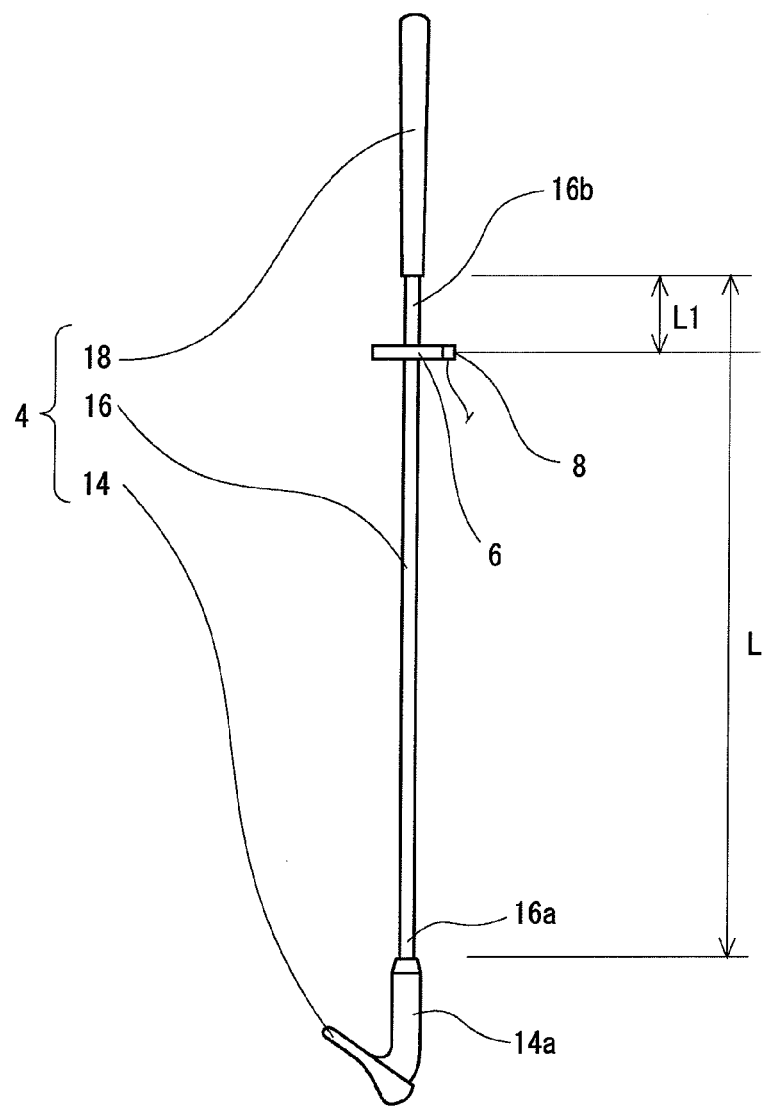
FIG. 2 is an illustration showing a golf club, a fitting jig, and a sensor of FIG. 1.

As shown in FIG. 2, the golf club 4 has a head 14, a shaft 16, and a grip 18. Unless otherwise mentioned, the description will be given assuming that the side close to a toe of the head 14 is a front end, and the side close to an end of the grip 18 is a back end. The head 14 is attached to a front end portion 16a of the shaft 16. The grip 18 is attached to a back end portion 16b of the shaft 16. A double-headed arrow L in FIG. 2 shows length from a back end of a hosel 14a of the head 14 to a front end of the grip 18.

With the golf club 4 as an example, FIG. 2 shows a holding section, a hitting section, and a shaft section of a sport hitting tool. The grip 18 is an example of the holding section to be held by a person P. The head 14 is an example of the hitting section for hitting a ball 20. The shaft 16 is an example of a shaft section connecting the head 14 as the hitting section with a grip 18 as the holding section.

The fitting jig 6 (not shown) includes a fitting jig body and a clamp, for example. The fitting jig body and the clamp sandwich the shaft 16. The fitting jig body and the clamp are fastened by screws. With this, the fitting jig body and the clamp are fixed, sandwiching the shaft 16. The fitting jig 6 is attached to the shaft 16 and fixed in this manner.

The sensor 8 is a three-axis accelerometer, for example. The three-axis accelerometer can measure acceleration in three axis directions: an X-axis direction, a Y-axis direction, and a Z-axis direction. The X-axis direction is an axial direction (up-down direction in FIG. 2) of the shaft 16. The Z-axis direction is a direction which is perpendicular to the X-axis direction and parallel to a hitting direction (right-left direction in FIG. 2). The Y-axis direction is a direction perpendicular to the X-axis and Z-axis directions (direction perpendicular to the sheet surface of FIG. 2). The sensor 8 is fixed to the fitting jig 6. The double-headed arrow L1 in FIG. 2 shows length from a position where the sensor 8 is attached, to a front end of the grip 18 in the axial direction of the shaft 16.

When the sensor 8 and the fitting jig 6 come into contact with the grip 18, the grip 18 alleviates vibration. The alleviation deteriorates measurement accuracy. From this standpoint, it is preferable that the sensor 8 and the fitting jig 6 are positioned, spaced from the grip 18. The spacing length is preferably equal to or greater than 0.5 mm, and more preferably equal to or greater than 1.0 mm.

On the one hand, when the sensor 8 and the fitting jig 6 come into contact with the head 14, vibration of the head 14 is measured. The vibration of the head 14 is vibration that is not directly transmitted to hands of the person P. When vibration of the head 14 is measured, the measurement accuracy of the sensor 8 deteriorates. From this standpoint, it is preferable that the sensor 8 and the fitting jig 6 are positioned, spaced from the head 14. The spacing length is preferably equal to or greater than 0.5 mm and more preferably equal to or greater than 1.0 mm.

Furthermore, it is preferable that the sensor 8 is measured, positioned close to hands. If the sensor 8 is measured, positioned close to hands, measurement data which is close to feeling of the person P can be obtained. Therefore, it is preferable that the sensor 8 is attached to a position close to the grip 18. From this standpoint, a ratio of the length L1 to the length L (L1/L) is preferably equal to or smaller than 0.75, more preferably equal to or smaller than 0.5, and particularly preferably equal to or smaller than 0.25.

Figure 3:
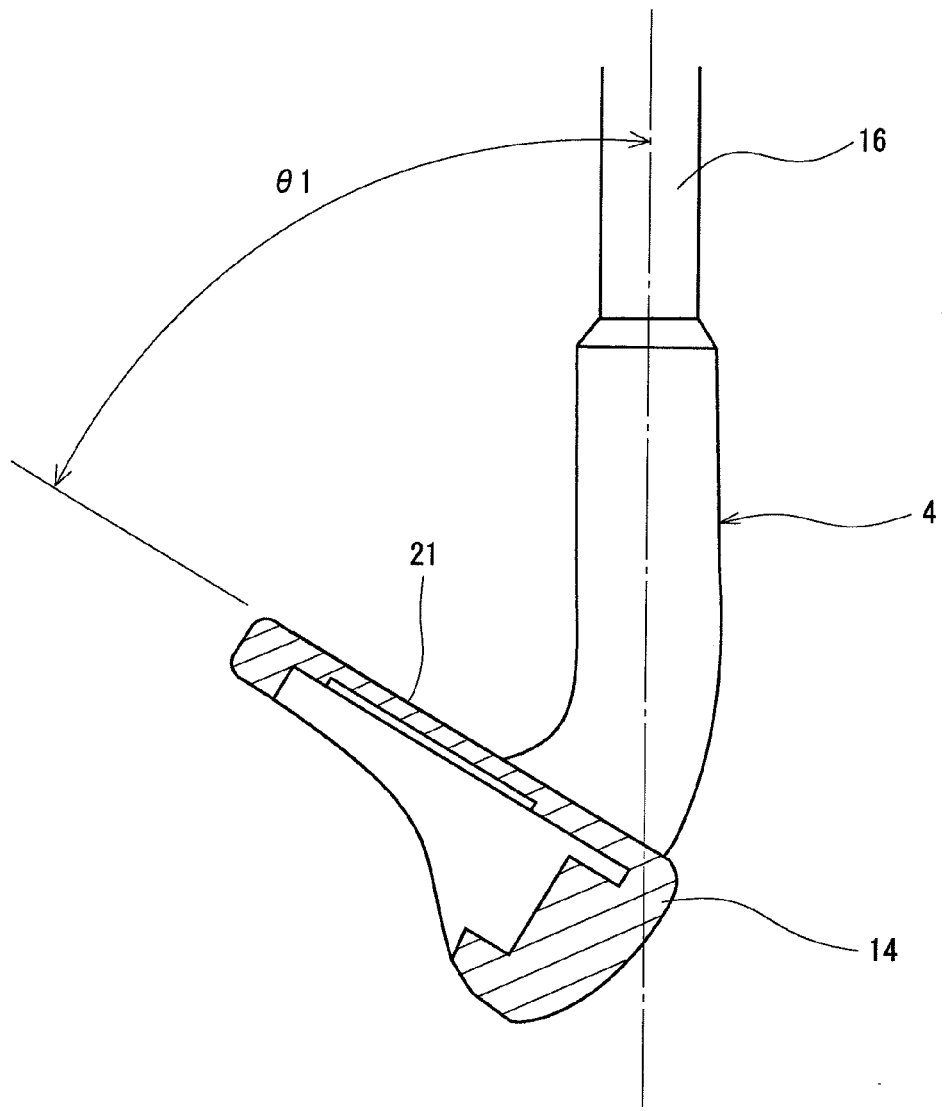
FIG. 3 is a partial enlarged view of the golf club of FIG. 2.

FIG. 3 shows a head 14 of a golf club 4. A double-headed arrow θ1 of FIG. 3 is an angle made by an axial direction of a shaft 16 and a face surface 21 which is an impact face. The angle θ1 represents a loft angle. In the golf club 4, the face surface 21 is inclined with respect to the axial direction of the shaft 16. Golf clubs include a wood type golf club, an iron type golf club, and the like. The golf club 4 in FIG. 3 is an iron type golf club. A set of golf clubs includes multiple golf clubs whose loft angles θ1 are different. In general, the loft angle θ1 is in a range from 8° to 65°.

The golf club 4 in FIG. 3 shows a wedge. Among the set of golf clubs, a large loft angle θ1 is set for a wedge. In general, a loft angle of an iron type golf club is in a range from 15° to 65°. The loft angle θ1 of the wedge is in a range from 40° to 65°.

Figure 4:
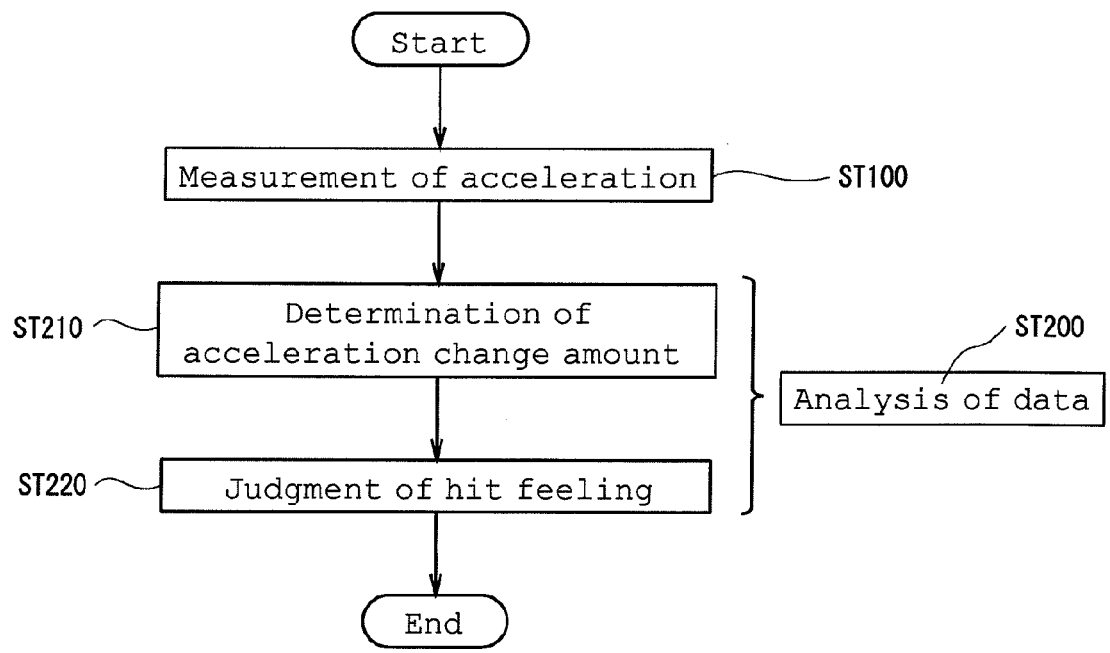
FIG. 4 is a flowchart for describing a procedure for the evaluation method according to the one embodiment of the present invention.

FIG. 4 shows a flow chart of the evaluation method for hit feeling. An acceleration measurement step (ST100) and a data analysis step (ST200) will be described with reference to FIG. 1.

In the acceleration measurement step (ST100), a swing subject is the person P, as shown in FIG. 1. In the acceleration measurement step (ST100), a swing robot may be used as a swing subject. When the swing robot is used, the swing robot holds a grip 18, which is the holding section, and makes a swing. For example, if universal hit feeling which is common to a number of persons is evaluated, the swing robot is effective. The swing robot is effective to capture the universal hit feeling as it has less fluctuation in each swing.

A controller 10 transmits a measurement start signal to the sensor 8. The golf club 4 is swung and the ball 20 is hit. During the swing, the sensor 8 measures acceleration in three directions of acceleration Ax in an X-axis direction, acceleration Ay in a Y-axis direction, and acceleration Az in a Z-axis direction. In the measurement, acceleration data in the three directions is obtained as measurement data. The controller 10 receives acceleration data in the three directions. The controller 10 transmits the acceleration data in the three directions to an information processor 12.

Figure 5:
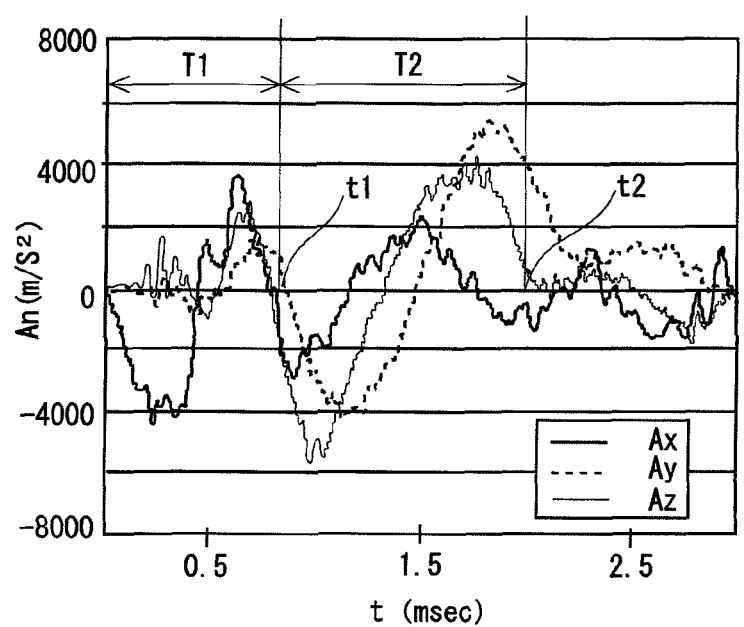
FIG. 5 is a graph showing one example of acceleration measured with the evaluation equipment of FIG. 1.

In FIG. 5, an example of acceleration data outputted to the information processor 12 is shown in a graph. FIG. 5 shows the acceleration Ax, the acceleration Ay, and the acceleration Az, respectively. A vertical axis of the graph in FIG. 5 is magnitude of acceleration An (where n is x, y, or z). A horizontal axis is measured time. The measured time is shown relative to hit time (t=0) when the ball 20 comes into contact with the golf club 4. In addition, any one of axial direction is may be a plus direction of acceleration, while the other may be a minus direction.

Double-headed arrows T1 and T2 represent measurement time in each interval. The time T1 represents time from the hit time (t=0) to time t1. In the time T1, the acceleration Ax returns to 0 after swinging to the minus direction once, and then returns to 0 again after further swinging to the plus direction. The time T1 represents a first cycle time of vibration of the acceleration Ax. Time T2 represents time from the time t1 to time t2. The time T2 represents time in a second cycle of the vibration.

As shown in FIG. 4, the data analysis step (ST200) includes an acceleration change amount determination step (ST210) and a hit feeling judgment step (ST220).

Figure 6:
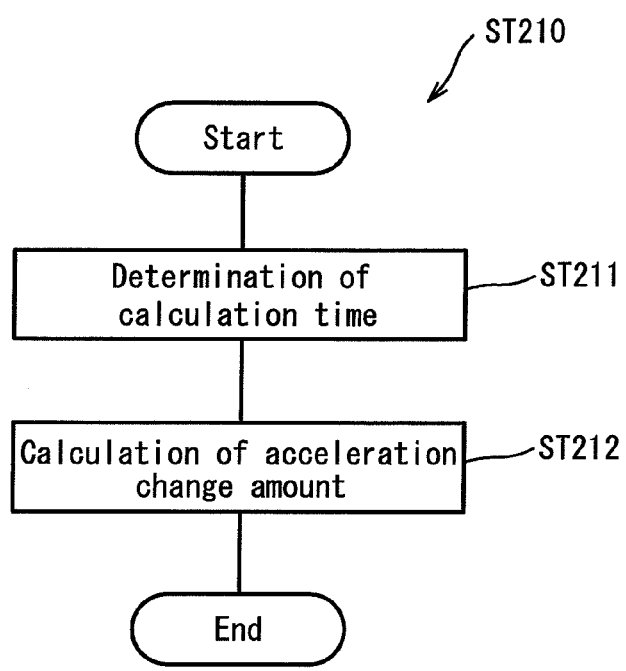
FIG. 6 is a flow chart for describing a procedure of an acceleration change amount determination step.

FIG. 6 shows the acceleration change amount determination step (ST210). In the acceleration change amount determination step (ST210), an amount of change in acceleration is determined from acceleration data. The acceleration change amount determination step (ST210) includes a calculation time determination step (ST211) and an acceleration change amount calculation step (ST212). Specifically, the time T1 of the first cycle is determined from the acceleration data shown in FIG. 5, for example. This is the calculation time determination step (ST211). For example, time for the acceleration Ax to return to 0 after once swinging to the minus direction (or plus direction) and then to return to 0 after further swinging to the plus direction (or minus direction) is determined as time T1.

An amount of change in acceleration is calculated from acceleration data of the time T1. This is the acceleration change amount calculation step (ST212). Specifically, at the time T1, for example, a maximum value Axmax and a minimum value Axmin of the acceleration Ax are determined. A difference in the maximum value Axmax and the minimum value Axmin (Axmax−Axmin) is calculated. Similarly, a difference between a maximum value Aymax and a minimum value Aymin of the acceleration Ay in the Y-axis direction (Aymax−Aymin) is calculated. A difference between a maximum value Azmax and a minimum value Azmin of the acceleration Az in the Z-direction is calculated. A sum value of the difference (Axmax−Axmin), the difference (Aymax−Aymin), and the difference (Azmax−Azmin) is calculated. The sum value is considered an amount of change in the acceleration.

In this example, time T1 is determined based on the first cycle of vibration determined from the acceleration Ax. On the basis of the time T1, maximum values and minimum values of the acceleration Ax, the acceleration Ay, and the acceleration Az are calculated. The time T1 may be determined based on a first cycle of vibration determined from the acceleration Ay, instead of the acceleration Ax. Similarly, the T1 may be determined based on a first cycle of vibration determined from the acceleration Az, instead of the acceleration Ax. Furthermore, the maximum value Axmax and the minimum value Axmin may be calculated based on the first cycle of vibration determined from the acceleration Ax, the maximum value Aymax and the minimum value Aymin may be calculated based on the first cycle of vibration determined from the acceleration Ay, and the maximum value Azmax and the minimum value Azmin may be calculated based on the first cycle of vibration determined from the acceleration Az.

In the hit feeling judgment step (ST220) shown in FIG. 4, hit feeling is judged using a calculated amount of change in acceleration. The larger the amount of change in acceleration is, the "harder" the hit feeling is evaluated to be. The smaller the amount of change in acceleration is, the "softer" the hit feeling is evaluated to be. For the judgment on hit feeling, multiple sport implements are prepared, for example. The sport implements are ranked from one with the "softest" hit feeling to one with the "hardest" hit feeling. In addition, as other example, the information processor 12 stores in advance thresholds for division into multiple ranks. The thresholds are compared with the calculated amount of change in acceleration. The hit feeling may be divided into five ranks, for example, and evaluated based on the thresholds.

Evaluation result in the hit feeling judgment step (ST220) is displayed in the output section, for example, display of the information processor 12, together with information on a measurement target.

Here, although the sum value of the difference (Axmax−Axmin), the difference (Aymax−Aymin), and the difference (Azmax−Azmin) were used as an amount of change in acceleration, an amount of change in acceleration is not limited to the sum value of the differences. The amount of change in acceleration may be a mean value of the difference (Axmax−Axmin), the difference (Aymax−Aymin), and the difference (Azmax−Azmin). The amount of change in acceleration may be a sum or a mean of the maximum values Axmax, Aymax, and Azmax, or a sum or a mean of the minimum values Axmin, Aymin, and Azmin.

In addition, although the amount of change in acceleration was calculated by using the acceleration Ax, the acceleration Ay, and the acceleration Az, it may be calculated by using the acceleration in any two axial directions of the acceleration Ax, the acceleration Ay, and the acceleration Az. In addition, the amount of change in acceleration may be calculated by using acceleration in an one axial direction of the acceleration Ax, the acceleration Ay, and the acceleration Az. If it is calculated by using the acceleration of one axial direction, a one-axis acceleration sensor may be used instead of a three-axis acceleration sensor.

When there is two vibrations or more in a very short time equal to or shorter than 10 msec, the person P perceives the vibrations as one vibration. As shown by results of tests 1 to 3 to be described below, a correlation of an amount of change in acceleration obtained in a first cycle of vibration and qualitative evaluation result by the person P is stronger than a correlation of an amount of change in acceleration obtained in a second cycle and the qualitative evaluation result by the person P. Accordingly, the evaluation method makes an evaluation using the amount of change in acceleration in the first cycle of vibration after hitting. This allows even a small difference, which cannot be adequately evaluated by a conventional qualitative evaluation method, to be qualitatively evaluated similarly to sensuous evaluation.

In the data analysis step, an amount of change in acceleration may be determined from acceleration measured in predetermined time which is defined in advance. It is preferable that the predetermined time is set so that an amount of change in acceleration in the first cycle is mainly determined. From this standpoint, preferably, the predetermined time is equal to or shorter than 1.5 msec after hitting. The predetermined time is more preferably equal to or shorter than 1.0 msec after hitting, or more preferably equal to or shorter than 0.8 msec after hitting, and particularly preferably equal to or shorter than 0.6 msec after hitting. On the one hand, from the standpoint of measuring the amount of change in acceleration of the first cycle of vibration, the predetermined time is preferably equal to or longer than 0.3 msec after hitting.

Figure 14:
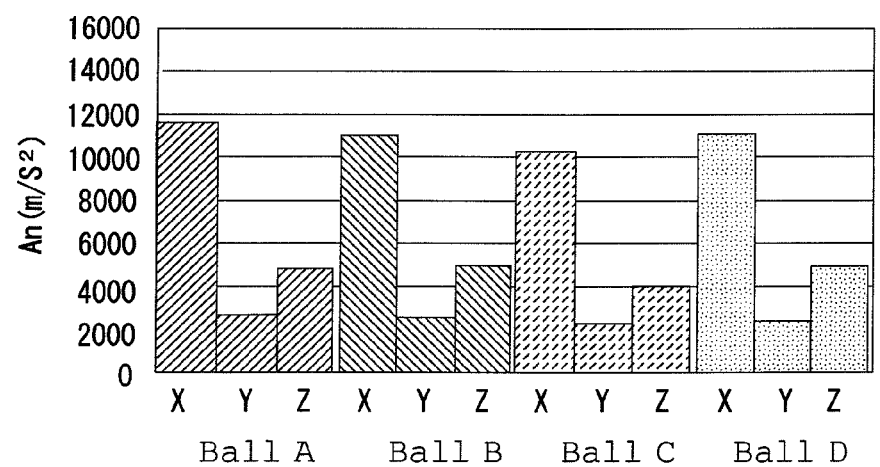
FIG. 14 is a graph showing an amount of change in acceleration in a first cycle of vibration after hitting for determining the evaluation result of FIG. 13(b).

As shown in FIG. 14 to be shown below, in the evaluation method using the golf club 4 in FIG. 1, the amount of change in acceleration Ax in the axial direction of the shaft 16 is greater than the amount of change in the acceleration Ay or the acceleration Az. The great amount of change has a huge impact on results of qualitative evaluations. From this standpoint, it is preferable that the hit feeling is evaluated by using an amount of change in the acceleration Ax.

Similarly, when an amount of change in acceleration is calculated by using acceleration of any two axial directions of the acceleration Ax, the acceleration Ay, and the acceleration Az, it is preferably calculated by using at least the acceleration Ax. In this evaluation method, it is most preferable that an amount of change in acceleration is calculated using the amounts of change in the three axial directions of the acceleration Ax, the acceleration Ay, and the acceleration Az.

Not only an amount of change in the acceleration Ax but also an amount of change in the acceleration Ay and an amount of change in the acceleration Az have an effect on hit feeling of the person P. From this standpoint, it is preferable that an amount of change in the acceleration is calculated by using two or more amounts of changes including at least an amount of change in the acceleration Ax, among an amount of change in the acceleration Ax, an amount of change in the acceleration Ay, and an amount of change in the acceleration Az. It is preferable, in particular, that an amount of change in the acceleration is calculated by using amounts of changes in the acceleration in the three axial directions of an amount of change in the acceleration Ax, an amount of change in the acceleration Ay, and an amount of change in the acceleration Az.

At the time T1, an amount of change in the acceleration Ax is large because the golf club 4 has the loft angle θ1. From this standpoint, the evaluation method for calculating an amount of change in acceleration by using at least acceleration Ax among the acceleration Ax, acceleration Ay, and acceleration Az is suitable for an evaluation method for hit feeling by using a golf club. The evaluation method is more suitable for evaluation of hit feeling by using a golf club with a large loft angle θ1. From this standpoint, the evaluation method is more suitable for evaluation of hit feeling by using an iron type golf club, and particularly suitable for evaluation by using a wedge.

In addition, the evaluation method is further suitable for evaluation of hit feeling by using a golf club with a loft angle θ1 being equal to or greater than 20°, and particularly suitable for evaluation of hit feeling by using a golf club with a loft angle θ1 being equal to or greater than 40°.

Figure 7:
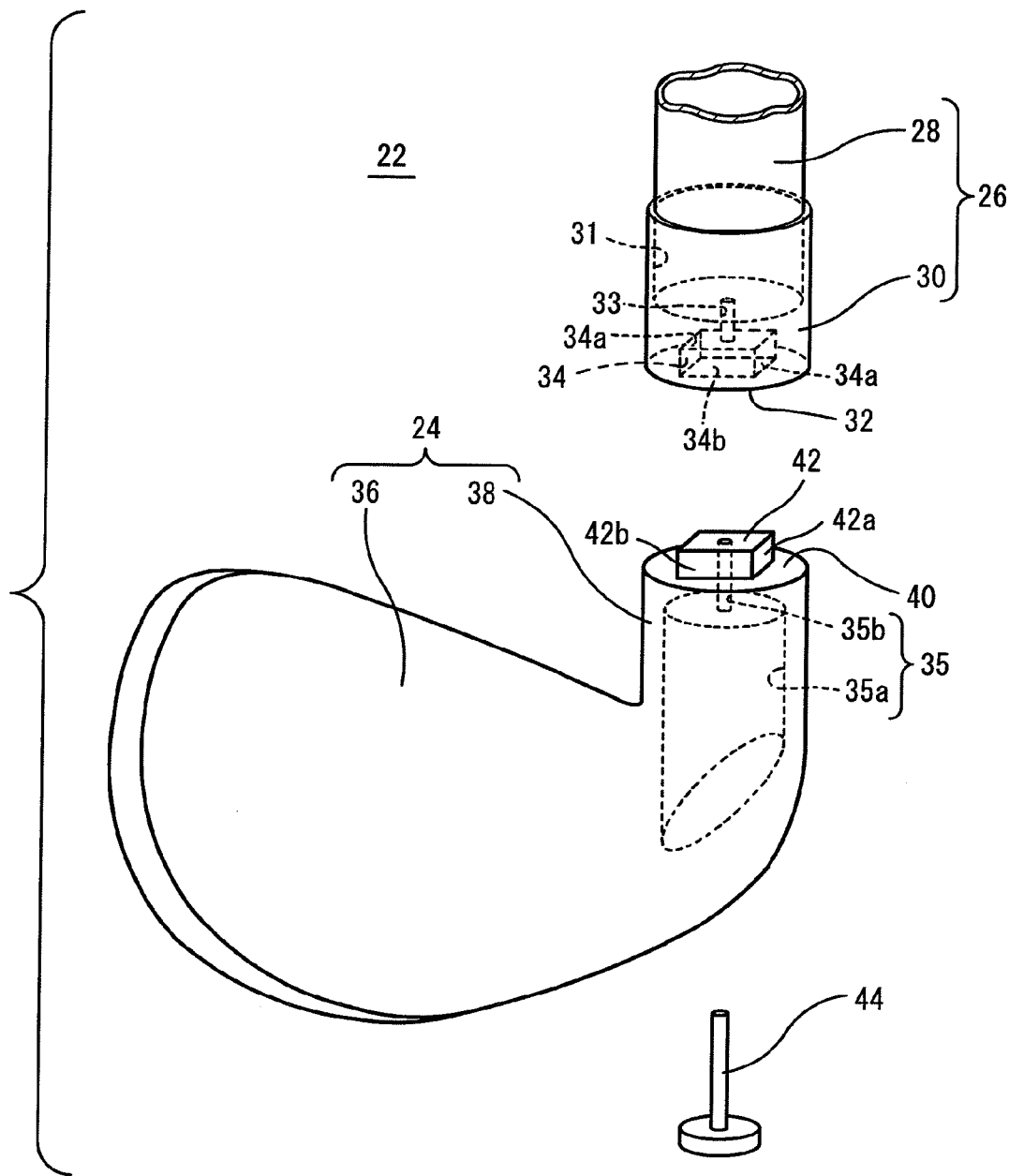
FIG. 7 is an illustration showing a part of a golf club used in an evaluation method according to another embodiment of the present invention.

FIG. 7 shows a part of a golf club 22 used in an evaluation method according to another embodiment of the present invention. Here, a configuration different from that of the golf club 4 will be described, and a description of a similar configuration will be omitted. In addition, configurations similar to the golf club 4, the fitting jig 6, the sensor 8, the controller 10, and the information processor 12, although they are not shown, will be described with the same numerals.

The golf club 22 has a head 24, a shaft 26, and a grip 18 (not shown). The shaft 26 has a shaft body 28 and an adapter 30. The adapter 30 is shaped like a circular cylinder. A bottomed insertion hole 31 is formed at a back end of the adapter 30. A front end of the shaft body 28 is inserted into the insertion hole 31 and fixed. A concave portion 34 is formed on an end face 32 at the front end of the adapter 30. A female screw 33 is formed on the bottom of the concave portion 34.

The head 24 has a head body 36 and a hosel 38. A convex portion 42 is formed on an end face 40 of the hosel 38. The convex portion 42 projects from the end face 40 in the shape of a rectangular solid. The convex portion 42 includes a planar surface 42a and a planar surface 42b which are parallel to an axial direction and orthogonal to each other. A through-hole 35 is formed on an axis line of the hosel 38. The through-hole 35 includes a large-diameter portion 35a and a small-diameter portion 35b which penetrates the convex portion 42 from a bottom of the large-diameter portion 35a.

The concave portion 34 of the adapter 30 has a shape to be associated and mate with the convex portion 42 of the hosel 38. The concave portion 34 includes a planar surface 34a which the planar surface 42*a* abuts, and a planar surface 34*b* which the planar surface 42*b* abuts. The convex portion 42 is inserted into the concave portion 34 and mate therewith. The end face 32 of the adapter 30 and the end face 40 of the hosel 38 are caused to abut each other. Screw 44 is inserted into the through-hole 35 and threaded into a female screw 33 of the adapter 30. With this, the head 24 is attached to the shaft 26.

The end face 32 abuts the end face 40, which thus positions the shaft 26 in the axial direction. The planar surface 34*a* abuts the planar surface 42*a*, and the planar surface 34*b* abuts the planar surface 42*b*, which thus positions the shaft 26 on a planar surface perpendicular to the axial direction and in a rotation direction with an axis of the shaft 26 as a rotation axis. The concave portion 34 and the convex portion 42 may be such shaped that they mate with each other, and that the shaft 26 is positioned on the planar surface perpendicular to the axial direction and positioned in the rotation direction with the axis of the shaft 26 as a rotation axis. Alternatively, a convex portion may be formed on the end face 32 and a concave portion may be formed on the end face 40.

An evaluation method according to another embodiment of the present invention will be described by using the golf club 22. The evaluation method also includes of an acceleration measurement step (ST100) and a data analysis step (ST200). This evaluation method for hit feeling differs from the evaluation method for hit feeling described above in the acceleration measurement step (ST100). Now, the acceleration measurement step (ST100) will be described.

Figure 8:
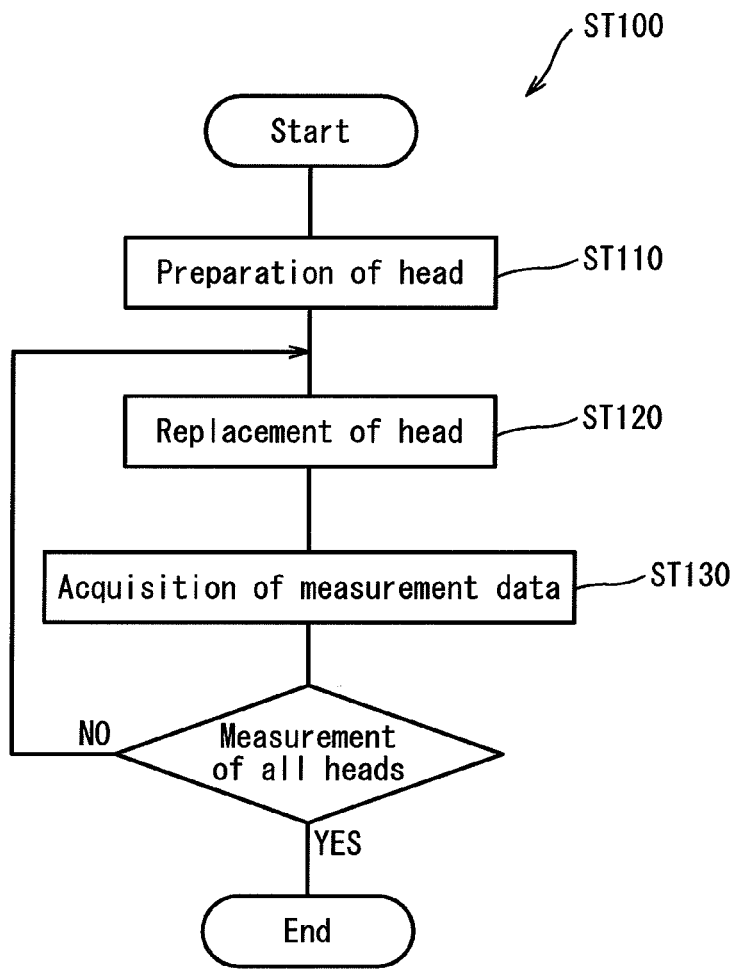
FIG. 8 is a flow chart for describing a procedure of an acceleration measurement step in an evaluation method using the golf club of FIG. 7.

As shown in FIG. 8, the acceleration measurement step (ST100) includes a head preparation step (ST110) as a hitting section preparation step, a head replacement step (ST120) as a hitting section replacement step, and a measurement data acquisition step (ST130).

A head 24 as one head, and a head H1 as other head and a head H2 as further other head (not shown), are prepared. This is the head preparation step (ST110). For example, the head 24, the head H1, and the head H2 are made different materials from each other. Their head shapes may be different from each other. Similar to the head 24, both head H1 and head H2 have the end face 40 and the convex portion 42. The head H1 and the head H2 are also configured so as to be detachable to the shaft 26.

Although it is not shown in FIG. 8, first, a swing robot swings a golf club 22, and acceleration data is obtained. Specifically, the head 24 is attached to the shaft 26. The attachment of the head 24 may be done before, during or after the head preparation step (ST110). The swing robot holds the grip, which is the holding section. A controller 10 transmits a measurement start signal to a sensor 8. The golf club 22 is swung and a ball 20 is hit. During the swing, the sensor 8 measures acceleration Ax, acceleration Ay, and acceleration Az. The controller 10 receives acceleration data of the three axis directions. The controller 10 transmits the acceleration data to the information processor 12.

After acceleration data of the head 24 is obtained, the head 24 is removed, and the head H1 is attached to the shaft 26. The head replacement is carried out in the state where the swing robot is holding the grip 18. This is the head replacement step (ST120).

The controller 10 transmits a measurement start signal to the sensor 8. The golf club provided with the head H1 is swung and the ball 20 is hit. During the swing, the sensor 8 measures acceleration Ax, acceleration Ay, and acceleration Az. The controller 10 receives acceleration data of the three axis directions. The controller 10 transmits the acceleration data to the information processor 12. This is the measurement data acquisition step (ST130).

Next, it is determined that whether measurement data has been obtained for all the heads prepared. Here, acceleration data has not been obtained for the head H2. Thus, it is determined that the acceleration data has not been obtained for all the heads, and the acceleration measurement step (ST100) returns to the head replacement step (ST120). In addition, a determination on whether acceleration data has been obtained for all heads may be made by a person or the information processor 12.

In the head replacement step (ST120), the head H1 is removed from the shaft 26. The head H2 is attached to the shaft 26. The head replacement is performed in the state where the swing robot is holding the grip 18.

Similar to the case of the head H1 described above, the controller 10 transmits a measurement start signal to the sensor 8 in the measurement data acquisition step (ST130). The golf club provided with the head H2 is swung and the ball 20 is hit. During the swing, the sensor 8 measures acceleration Ax, acceleration Ay, and acceleration Az. The controller 10 receives acceleration data of the three axis directions. The controller 10 transmits the acceleration data to the information processor 12.

In the example, when acceleration data is obtained for the head H1 and the head H2, it is determined that the acceleration data has been obtained for all the heads. With this, the acceleration measurement step (ST100) ends.

If still other head is prepared, the acceleration measurement step (ST100) returns to the head replacement step (ST120). The head replacement step (ST120) and the measurement data acquisition step (ST130) are repeated in this manner until acceleration data is obtained for all the heads. If it is determined that the acceleration data has been obtained for all the heads, the acceleration measurement step (ST100) ends.

As the swing robot is used in the method, acceleration data with constant swings can be obtained. The constant swings inhibit fluctuations in measurement result. In the evaluation method for hit feeling, evaluation of the head 24, the head H1, and the head H2 is performed only with the head replacement. In the head replacement, the holding state of the grip 18 by the swing robot and the attachment state of the sensor 8 are kept as they are. The evaluation method eliminates a need for adjustment of positioning with the swing robot and the grip 18. It eliminates a need for adjustment of attachment state of the sensor 8. The evaluation method has fewer factors for fluctuations in measurement. The evaluation method enables measurement result showing small fluctuations to be obtained.

The end face 32 abuts the end face 40, and the concave portion 34 mates with the convex portion 42. This facilitates positioning of the head 24, the head H1, and the head H2 with respect to the shaft 26. Multiple different heads are similarly attached to the shaft 26 in predetermined postures. As attachment postures of the shaft 26 and the head 24, and of the head H1 and the head H2 are predetermined postures, measurement result showing small fluctuations can be obtained more easily.

Here, although the description was given taking the replacement of the head 24, the head H1, and the head H2 as an example, the quality of heads may be evaluated for multiple identical heads prepared. In addition, the description was given based on the configuration of the golf club 22 shown in FIG. 7, an attachment structure of the shaft 26 and the head 24 is not limited to this configuration. The attachment structure may be an attachment structure of a golf club 46 in FIG. 9, a golf club 48 in FIG. 10, and a golf club 50 in FIG. 11 to be described below.

Figure 9:
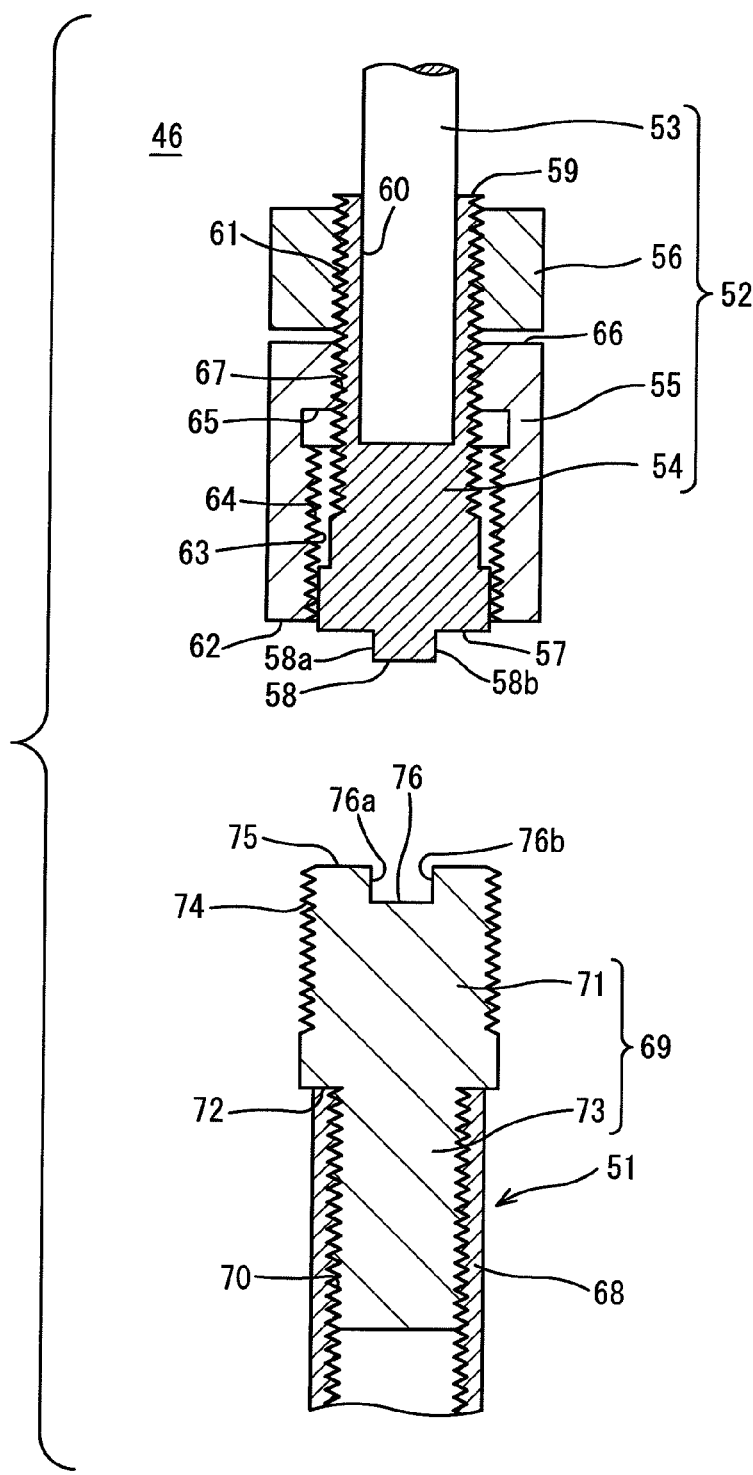
FIG. 9 is an illustration showing a part of a golf club used in an evaluation method according to still another embodiment of the present invention.

The golf club 46 in FIG. 9 has a head 51, a shaft 52, and a grip 18 (not shown). The shaft 52 has a shaft body 53, a shaft adapter 54, a connecting nut 55, and a locking nut 56.

A convex portion 58 is formed on an end face 57 at the front end of shaft adapter 54. The convex portion 58 has planar surfaces 58a and 58b parallel to an axis line of the shaft 52. An insertion hole 60 is formed on an end face 59 at a back end of the shaft adapter 54. A male screw 61 is formed on a back outer circumferential surface of the shaft adapter 54. A front end of the shaft body 53 is inserted into the insertion hole 60 and fixed.

A bottomed hole 63 is formed on an end face 62 at the front end of the connecting nut 55. A female screw 64 is formed on an inner circumferential surface of the hole 63. A female screw 67 penetrating an end face 66 at the back end is formed on a bottom face 65 of the hole 63. An effective diameter of the female screw 67 is smaller than the female screw 64. Pitch of the female screw 67 is identical to pitch of the female screw 64. The connecting nut 55 is attached to the shaft adapter 54 by threading the male screw 61 of the shaft adapter 54 into the female screw 67. The locking nut 56 is attached to the shaft adaptor 54 by threading the male screw 61 of the shaft adapter 54. The locking nut 56 faces the end face 66 of the connecting nut 55.

The head 51 has a head body (not shown), a hosel 68, and a head adapter 69. A female screw 70 is formed in the hosel 68. The head adapter 69 includes a head portion 71 almost shaped like a circular cylinder, and a male screw 73 projecting from an end face 72 at the front end side of the head portion 71. A male screw 74 is formed on an outer circumferential surface of the head portion 71. A concave portion 76 is formed on an end face 75 at the back end of the head portion 71. The concave portion 76 has planar surfaces 76a and 76b parallel to an axis line of the hosel 68. The male screw 73 being screwed into the female screw 70, the head adapter 69 is fixed to the hosel 68.

The concave portion 76 has a shape to be associated and mate with the convex portion 58 of the shaft adapter 54. A planar surface 58a of the convex portion 58 abuts the planar surface 76a of the concave portion 76. A planar surface 58b abuts the planar surface 76b. The end face 57 of the shaft adapter 54 abuts the end face 75 of the head adapter 69. The male screw 74 of the head adapter 69 being threaded into the female screw 64 of the connecting nut 55, the head 51 is attached to the shaft 52. Furthermore, the male screw 61 of the shaft adapter 54 being threaded into the locking nut 56, the locking nut 56 is caused to abut the connecting nut 55. This prevents the connecting nut 55 from loosening.

In the golf club 46, the end face 57 abutting the end face 75, the shaft 52 is positioned in an axial direction. The planar surface 76a abutting the planar surface 58a and the planar surface 76b abutting the planar surface 58b, the shaft 52 is positioned in a rotation direction with an axis of the shaft 52 as a rotation axis. Mating of the concave portion 76 with the convex portion 58 facilitates definition of orientation of the face surface of the head 51.

Figure 10:
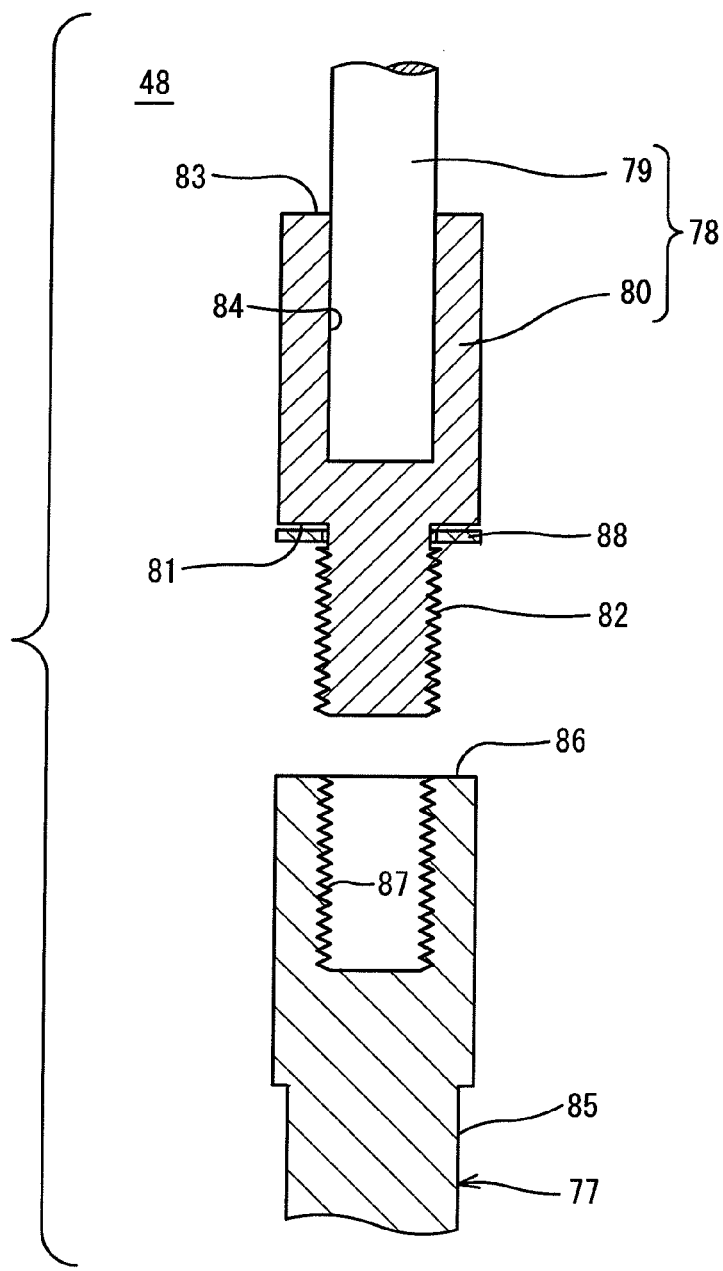
FIG. 10 is an illustration showing a part of a golf club used in an evaluation method according to further another embodiment of the present invention.

The golf club 48 in FIG. 10 has a head 77, a shaft 78, and a grip 18 (not shown). The shaft 78 has a shaft body 79 and an adapter 80. The adapter 80 is shaped almost like a circular cylinder, and has a male screw 82 projecting from an end face 81 on the front end side. An insertion hole 84 is formed on an end face 83 on the back end side of the adapter 80. A front end of the shaft body 79 is inserted into the insertion hole 84 and fixed.

The head 77 has a head body (not shown), and a hosel 85. A female screw 87 is formed in a screw hole of an end face 86 of the hosel 85. The male screw 82 of the adapter 80 being threaded into the female screw 87, the head 77 is attached to the shaft 78. In the golf club 48, a lock washer 88 is sandwiched between an end face 81 of the adapter 80 and an end face 86 of the hosel 85, thereby preventing loosening. In the golf club 48, the head 77 is fixed to the shaft 78 with a relatively simple structure.

Figure 11:
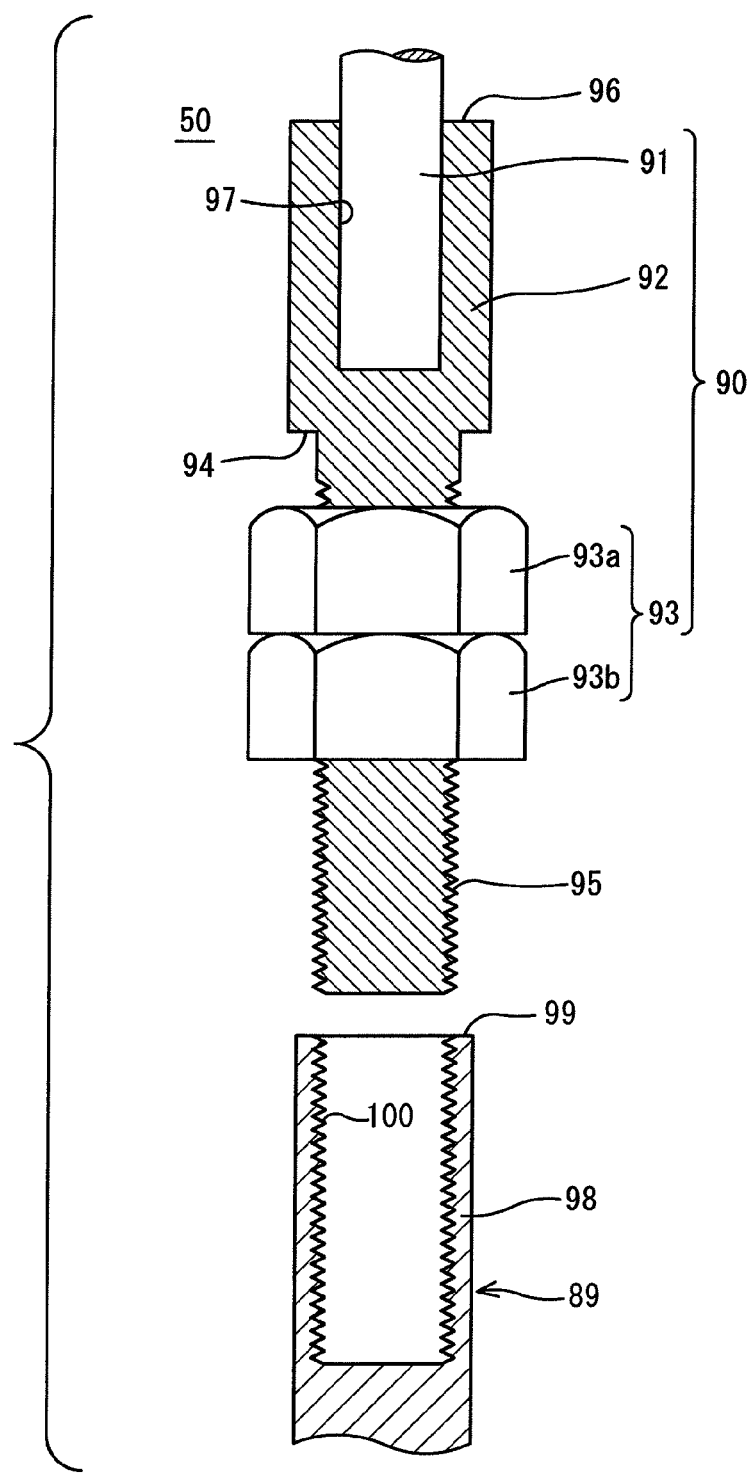
FIG. 11 is an illustration showing a part of a golf club used in an evaluation method according to yet another embodiment of the present invention.

The golf club 50 of FIG. 11 has a head 89, a shaft 90, and a grip 18 (not shown). The shaft 90 has a shaft body 91, an adapter 92 and lock nuts 93 (93a, 93b). The adapter 92 is shaped almost like a circular cylinder, and has a male screw 95 projecting from an end face 94 on the front end side. An insertion hole 97 is formed on an end face 96 at the back end side of the adapter 92. A front end of the shaft body 91 is inserted into the insertion hole 97 and fixed. The male screw 95 is threaded into the lock nuts 93 (93a, 93b).

The head 89 has a head body (not shown), and a hosel 98. A female screw 100 is formed on an end face 99 of the hosel 98. The male screw 95 being threaded into the adapter 92 of the female screw 100, the head 89 is attached to the shaft 90. In this golf club 50, abutting an end face 99 of the hosel 98 with the male screw 95 being threaded into the lock nut 93, the lock nut 93 is prevented from loosening. The golf club 50 has a relatively simple structure, and the head 89 is fixed to the shaft 90.

Figure 12:
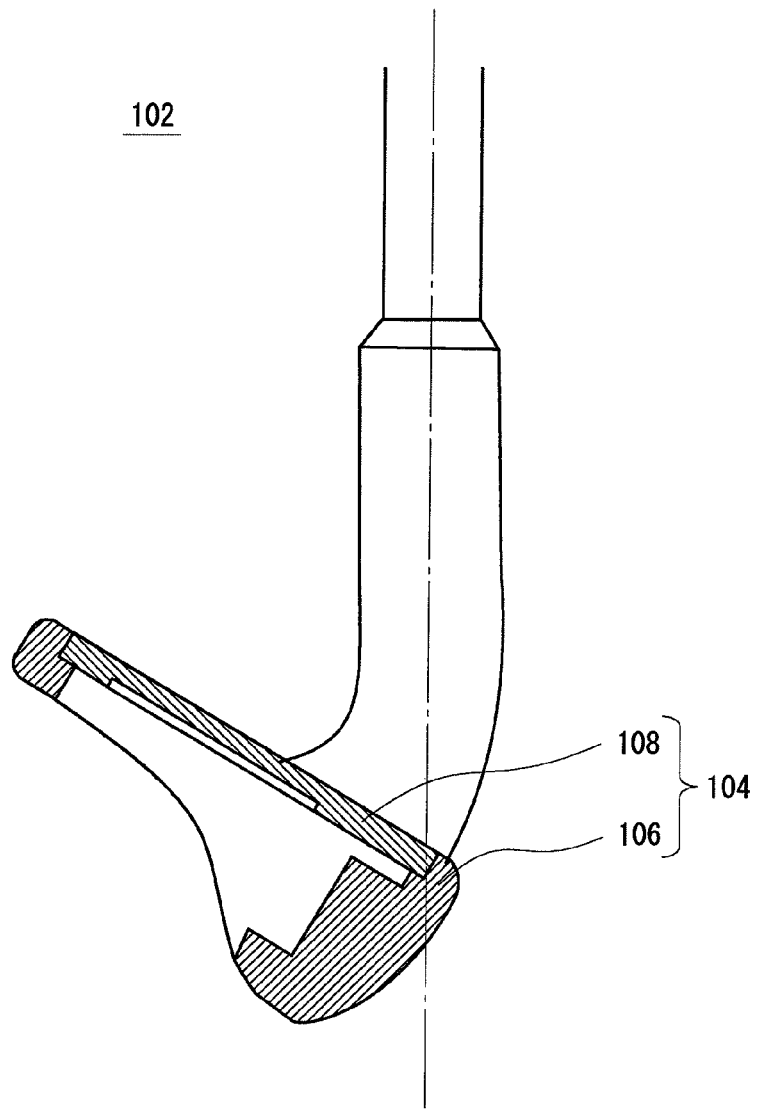
FIG. 12 is an illustration showing a part of a golf club used in an evaluation method according to still another embodiment of the present invention.

FIG. 12 shows a part of a golf club 102 according to still another embodiment of the present invention. A head 104 has a head body 106 as a casing and a face 108 for hitting a ball. The face 108 is detachably attached to the head body 106. Although it is not shown, the face 108 is positioned and fixed to the head body 106. For example, the face 108 is mated with the head body 106.

An evaluation method for hit feeling by using the golf club 102 will be described. The evaluation method also includes an acceleration measurement step (ST100) and a data analysis step (ST200). The evaluation method for hit feeling differs from the evaluation method for hit feeling shown in FIG. 4 in the acceleration measurement step (ST100). Here, the acceleration measurement step (ST100) will be described.

Although it is not shown, the acceleration measurement step (ST100) includes a face preparation step, a face replacement step, and a measurement data acquisition step.

The face 108 as one face and other face F1 are prepared. This is the face preparation step. The face F1 is also configured to be detachably attached to the head body 106. The face 108 and the face F1 are made of different materials, for example. Alternatively, the face 108 and the face F1 may differ in thickness or in groove geometry of a face surface.

First, the face 108 is attached to the head body 106. The swing robot holds the golf club 102. The swing robot swings with the golf club 102. A controller 10 transmits a measurement start signal to the sensor 8. The golf club 102 is swung and the ball 20 is hit. During the swing, the sensor 8 measures acceleration Ax, acceleration Ay, and acceleration Az. The controller 10 receives acceleration data of the three axis directions. The controller 10 transmits the acceleration data to the information processor 12.

After acceleration data is obtained with the golf club 102, the face 108 is removed. The face F1 is attached to the head body 106 instead of the face 108. The face replacement is performed in a state where the swing robot is holding the grip 18. This is the face replacement step.

The golf club to which the face F1 is attached is swung and the ball 20 is hit. During the swing, the sensor 8 measures acceleration. Ax, acceleration Ay, and acceleration Az. The controller 10 receives acceleration data of the three axis directions. The controller 10 transmits the acceleration data to the information processor 12. This is the measurement data acquisition step.

Next, it will be determined whether measurement data has been obtained for all the faces prepared. Unless the acceleration data has been obtained for all the faces, the step returns to the face replacement step. Here, acceleration data has been obtained for the face F1 prepared. As the acceleration data has been obtained for all the faces, the measurement data acquisition step ends.

In the evaluation method for hit feeling, evaluation of hit feeling of the face 108 and the face F1 is performed only through the face replacement. In the replacement, the holding state of the grip 18 by the swing robot is kept as it is. The attachment state of the sensor 8 is also kept as it is. The evaluation method eliminates a need for adjustment of positioning of the swing robot and the grip 18. The evaluation method has fewer factors for fluctuations in measurement. The evaluation method enables measurement result showing small fluctuations to be obtained easily. The evaluation method is advantageous for evaluation of hit feeling. The evaluation method is advantageous for evaluation of hit feeling, in particular, in terms of face materials, thickness, and groove geometry of a face surface. Here, although the description was given taking the replacement of the face 108 and the different face as an example, the face quality may be evaluated for multiple identical faces prepared.

In the following, although Examples reveal effects of the present invention, the present invention should not be interpreted as limited, based on the description of the Examples.

EXAMPLES

Hit feeling of golf balls was evaluated by Test 1 to Test 3. As shown in FIG. 1, in the tests, hit feeling of golf balls (hereinafter referred to as balls) was evaluated with a golf club. In the tests, as the golf club, sand wedge "ZR-800 SW" manufactured by SRI Sports Limited was used. As the balls, four types of balls, a ball A, a ball B, a ball C, and a ball D, were used. As a sensor, a three-axis accelerometer "356A01" manufactured by TOYO Corporation was used. A fitting jig on which the sensor is attached is fixed to the shaft of the golf club.

[Test 1]

Figure 13A:
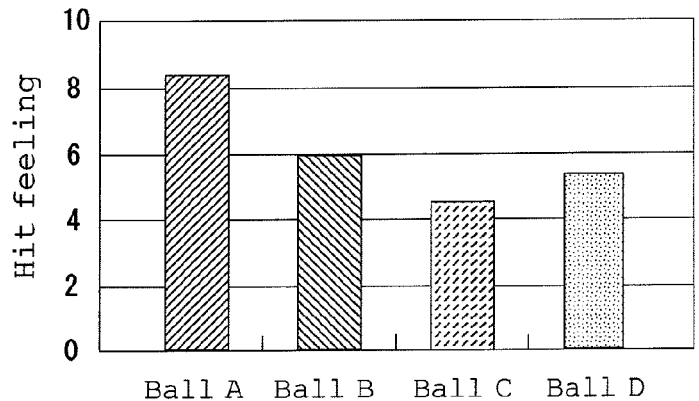
FIG. 13(a) is a graph showing evaluation result of hit feeling of sensuous evaluation.

Three high-level players hit each of the four types of balls on trial with the golf club. A sensuous evaluation of hit feeling of the trial hits was performed. In the sensuous evaluation, the hit feeling of the trial hits was evaluated in 10 stages. For results of the sensuous evaluations, a mean value of the three high-level players was determined. FIG. 13(a) shows the mean values. In the evaluation, the "harder" the hit feeling is, the larger the figures are, and the "softer" it is, the smaller the figures are.

[Test 2]

Figure 13B:
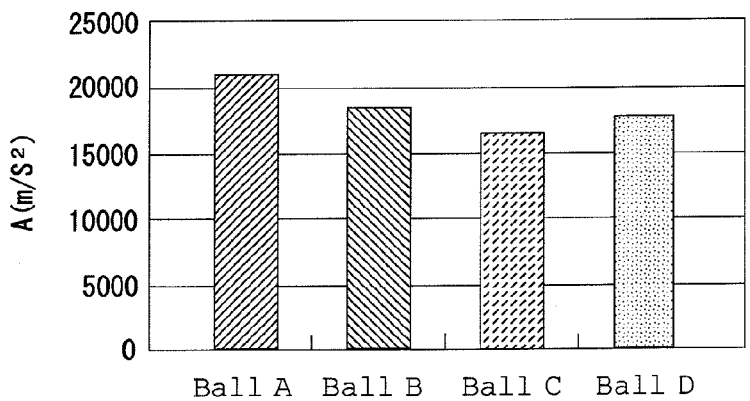
FIG. 13(b) is a graph showing evaluation result of hit feeling of an evaluation method according to one embodiment of the present invention.

The hit feeling was evaluated with the evaluation method of the present invention. In the acceleration measurement step, the same high-level players as those in the Test 1 hit each of the four types of balls on trial with the golf club. In swings of the trial hits, acceleration in the three-axis directions was measured. In the data analysis step, time T1 was determined based on a first cycle of vibration of the acceleration Ax obtained. An amount of change in the acceleration at the time T1 was calculated. The amount of change in the acceleration is a sum of a difference (Axmax−Axmin), a difference (Aymax−Aymin), and a difference (Azmax−Azmin). FIG. 13(b) shows the evaluation results. In the evaluation, the "harder" the hit feeling is, the larger the acceleration A (m/s$^2$) is, and the "softer" it is, the smaller the acceleration A (m/s$^2$) is.

[Test 3]

Figure 13C:
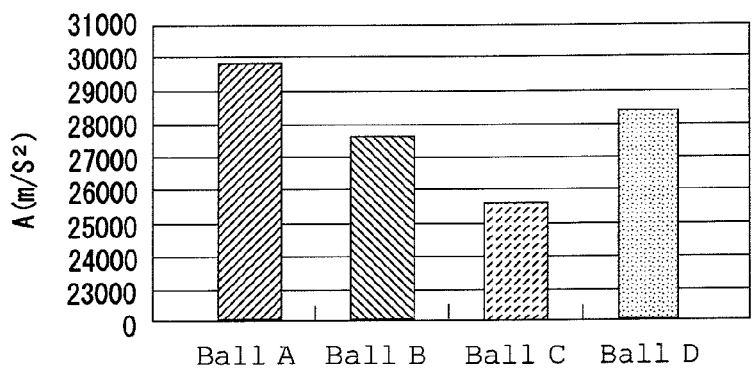
FIG. 13(c) is a graph showing evaluation result of hit feeling in a comparative example.

As a comparative example of the evaluation method of the present invention, hit feeling was evaluated with other method. In this evaluation method, acceleration data obtained in the Test 2 was used. In the data analysis step of the evaluation method, time T2 was determined based on a second cycle of vibration of the acceleration Ax. An amount of change in the acceleration at the time T2 was calculated. The evaluation was performed with other conditions set similarly to the Test 2. FIG. 13(c) shows the evaluation results thereof.

A same tendency was obtained from the result of the sensuous evaluation of FIG. 13(a) and evaluation result of FIG. 13(b). On the one hand, in the evaluation result of FIG. 13(c), the ball D was evaluated to be "harder" than the ball B. The same tendency was not obtained from the evaluation result of FIG. 13(c) and the result of the sensuous evaluation. A correlation of an amount of change in the acceleration obtained from the first cycle of vibration and result of qualitative evaluation of the person P is stronger than a correlation of an amount of change in acceleration obtained from the second cycle and the result of qualitative evaluation of the person P. From this evaluation result, the advantage of the evaluation method of the present invention is obvious.

FIG. 14 shows the amounts of change in the acceleration in FIG. 13(b) by dividing them into the three-axis directions. It shows the amounts of changes in acceleration for each of the four kinds of balls, by dividing them into a difference in the X-axis direction (Axmax-Axmin), a difference in the Y-axis direction (Aymax-Aymin), and a difference in the Z-Axis direction (Azmax-Azmin).

Figure 15:
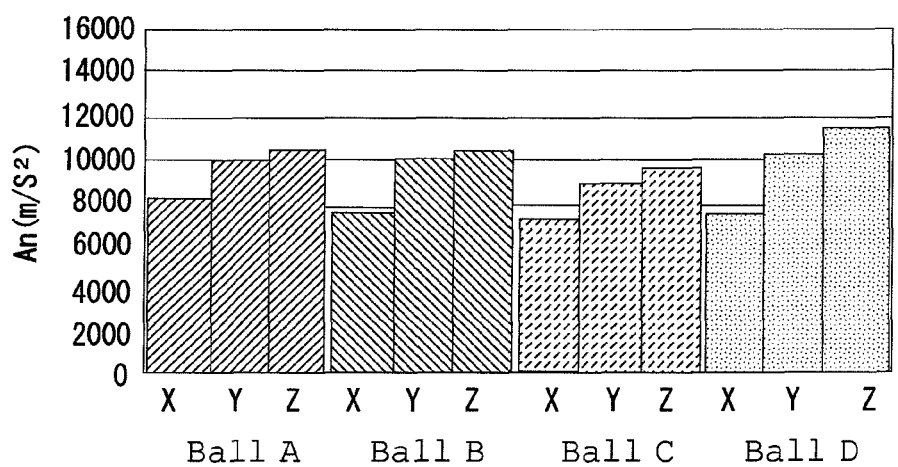
FIG. 15 is a graph showing an amount of change in acceleration of vibration after hitting for determining the evaluation result of FIG. 13(c).

FIG. 15 shows the amounts of change in the acceleration in FIG. 13(c) by dividing them into the three-axis directions. It shows the amounts of changes in acceleration for each of the four kinds of balls, by dividing them into a difference in the X-axis direction (Axmax-Axmin), a difference in the Y-axis direction (Aymax-Aymin), and a difference in the Z-Axis direction (Azmax-Azmin).

As shown in FIG. 14, at the time T1, the amount of change in the acceleration Ax is larger than the amount of change in the acceleration Ay and the amount of change in the acceleration Az. There is a big difference among the amount of change in the acceleration Ax, the amount of change in the acceleration Ay, and the amount of change in the acceleration Az. In contrast, as shown in FIG. 15, at the time T2, the amount of change in the acceleration Ax does not increase relative to the amount of change in the acceleration Ay and the amount of change in the acceleration Az. There is a small difference among the amount of change in the acceleration Ax, the amount of change in the acceleration Ay, and the amount of change in the acceleration Az. At the time T1, in the golf club, the amount of change in the acceleration Ax makes a great contribution to an amount of change in acceleration. From this standpoint, in the golf club, it is preferable that when an amount of change in acceleration is calculated, it is calculated using at least acceleration Ax.

Here, although the description was given taking as an example the evaluation of hit feeling of golf balls by using the four kinds of balls, this evaluation method is also used in evaluation of hit feeling of a golf club. Specifically, for example, hit feeling of a golf club can be evaluated by hitting one golf ball with multiple golf clubs.

Hit feeling of golf clubs was evaluated by Test 4 to Test 6. In the tests, golf clubs provided with the configuration shown in FIG. 7 were used and evaluation was performed.

[Test 4]

Reproducibility of hit feeling was evaluated by using the golf club in FIG. 7. For the test, a shaft, a head A, a ball E, and a swing robot were prepared. The shaft and the head A was provided with the configuration shown in FIG. 7. As the head A, a SUS cast head ("CG15 Black Pearl Tour Zip Grooves" manufactured by Cleveland Golf Company, Inc.) was used. As the ball E, "Z-STAR XV" manufactured by SRI Sports Limited was used. As a sensor, a three-axis accelerometer "356A01" manufactured by TOYO Corporation was used. As a swing robot, "Hitting Machine" manufactured by Golf Laboratories Inc. was used.

The shaft had a shaft body and an adapter. As the shaft body, "DG S200" manufactured by True Temper Sports, Inc. was used. A concave portion was formed on an end face at the front end of the adapter. A convex portion was formed on an end face of a hosel of the head A. The concave portion of the adapter and the convex portion of the hosel were screw connected while being mated. With this, the head A was detachably attached to the shaft.

The golf club was attached to the swing robot. The swing robot swung the golf club and hit the ball E. The head speed of the swing was set to 21 m/sec. For the hitting, acceleration in three directions was measured. An amount of change in the acceleration was calculated from the measured acceleration. The amount of change in acceleration is a sum of a difference (Axmax−Axmin), a difference (Aymax−Aymin), and a difference (Azmax−Azmin). The amount of change in the acceleration was determined at time T1 in a first cycle of vibration of the acceleration Ax. A set consisting of the measurement of acceleration and the calculation of the amount of change in acceleration from the measured acceleration was repeated eight times. A mean value of the measured amounts of changes in the acceleration for eight times was determined. The determined mean value was considered a mean value for the first time.

Figure 16:
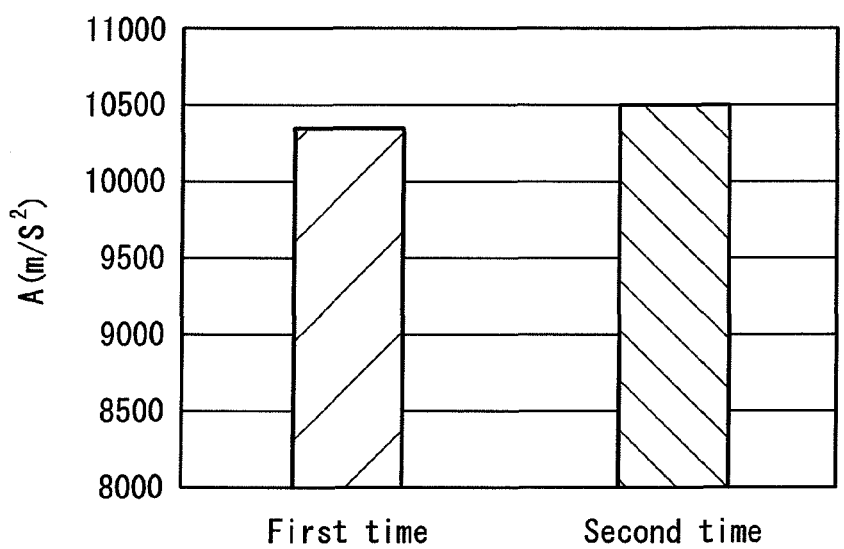
FIG. 16 is a graph showing evaluation result of hit feeling using the golf club of FIG. 7.

After the mean value of the first time was determined, the head A was removed from the shaft. The head A was attached to the shaft again. A mean value of the amounts of changes in acceleration for the second time was determined with the same method as the method with which the mean value for the first time was determined. FIG. 16 shows the mean value for the first time and the mean value for the second time.

As shown in FIG. 16, a difference between the mean value for the first time and the mean value for the second time was smaller than 200 m/s². The difference in the mean values was less than 2% of the obtained amount A of change in acceleration (m/s²). In the evaluation method in which only the heads were replaced, high reproducibility was found in the amount of change in acceleration. The evaluation method by the replacement of heads only enables evaluation result showing small fluctuations to be obtained easily. The evaluation method is advantageous, when a difference in hit feeling is small, as fluctuations in evaluation results are small. The evaluation method is advantageous, in particular, for evaluation of hit feeling based on head differences, such as a difference in a manufacturing method, a material, a shape, and a structure of heads.

[Test 5-1]

In the test, a head B was used in addition to the shaft, the sensor, the head A, and the ball E used in the Test 4. Similar to the head A, the head B has the configuration of the head shown in FIG. 7. As the head B, a soft iron forged head ("CG15 Forged" manufactured by Cleveland Golf Company, Inc.) was used.

Figure 17A:
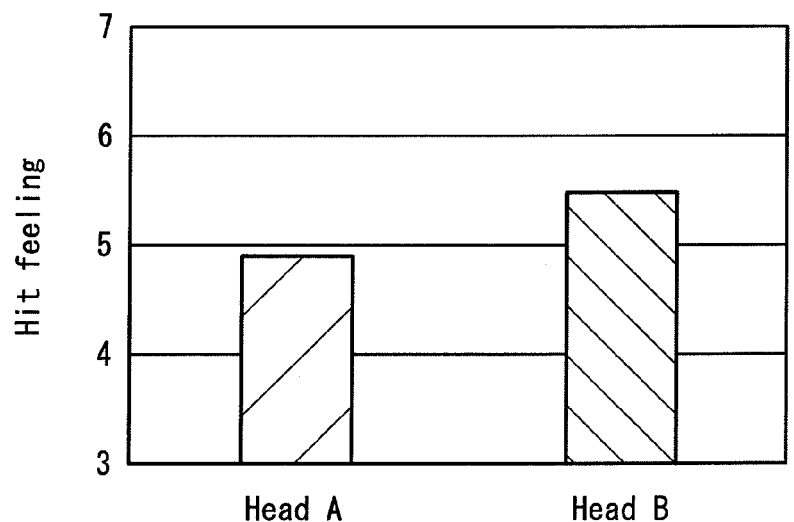
FIG. 17(a) and FIG. 17(b) are graphs showing evaluation result of hit feeling of sensuous evaluation using the golf club of FIG. 7.

The head A was attached to the shaft. Ten high-level players hit the ball E on trial with the golf club to which the head A was attached. The head speed of the swing was adjusted to 21 m/sec. Each high-level players hit eight times and a sensuous evaluation of their hit feeling was performed. A mean value of the sensuous evaluations for the 10 persons was determined. FIG. 17(a) shows the mean value. The hit feeling was evaluated in 10 stages. In the evaluation, the "harder" the hit feeling is, the larger the figure is, and the "softer" it is, the smaller the figure is.

[Test 5-2]

Figure 17B:
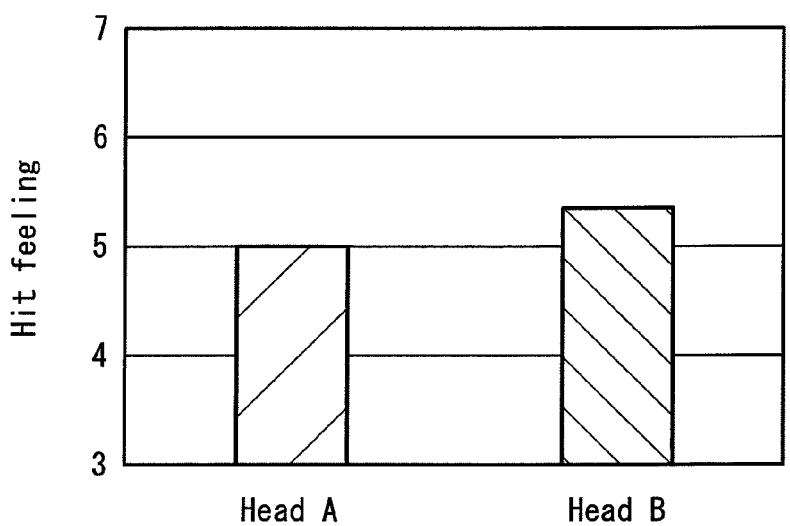

A mean value of sensuous evaluations was determined similarly to the Test 5-1, except that the head speed of swing was adjusted to 31 m/sec. FIG. 17(b) shows the mean value.

[Test 5-3]

The head A was removed from the shaft, and the head B was attached. A mean value of sensuous evaluations was determined similarly to the Test 5-1, except that the head B replaced the head A. FIG. 17(a) shows the mean value.

[Test 5-4]

A mean value of sensuous evaluations was determined similarly to the Test 5-2, except that the head B replaced the head A. FIG. 17(b) shows the mean value.

[Test 6-1]

Figure 18A:
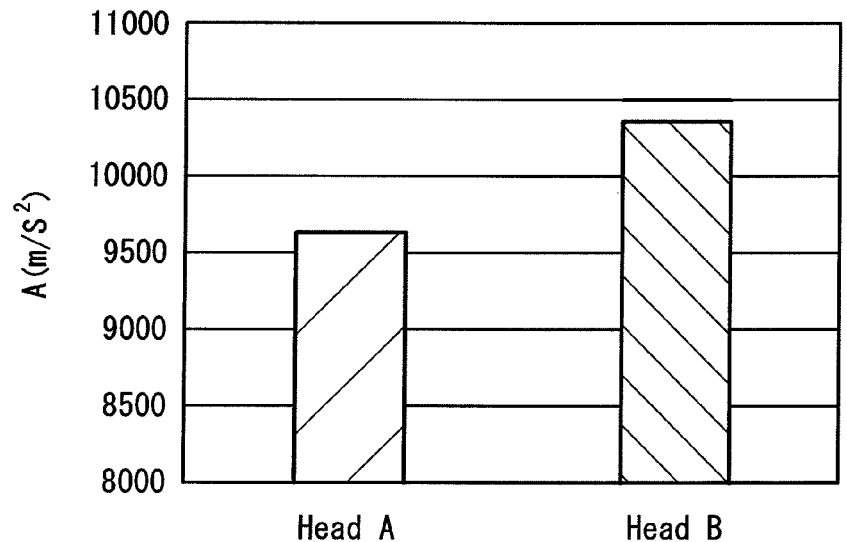
FIG. 18(a) and FIG. 18(b) are graphs showing evaluation result of hit feeling with the golf club of FIG. 7 and a swing robot.

The shaft, the sensor, the head A, the head B, and the ball E which were used in the Test 5 were used. Furthermore, the swing robot used in the Test 4 was prepared. The head A was attached to the shaft of the golf club. The swing robot hit the ball E on trial with the golf club. The head speed of the swing was set to 21 m/sec. From the trial hits, an amount of change in acceleration was calculated. The amount of change in the acceleration is a sum of a difference (Axmax−Axmin), a difference (Aymax−Aymin), and a difference (Azmax−Azmin). To calculate the amount of change in the acceleration, the measurement of the acceleration and the calculation of the amount of change in the acceleration from the measured acceleration were repeated eight times. The amount of change in the acceleration was determined as a mean value for the eight times. FIG. 18(a) shows the mean value.

[Test 6-2]

Figure 18B:
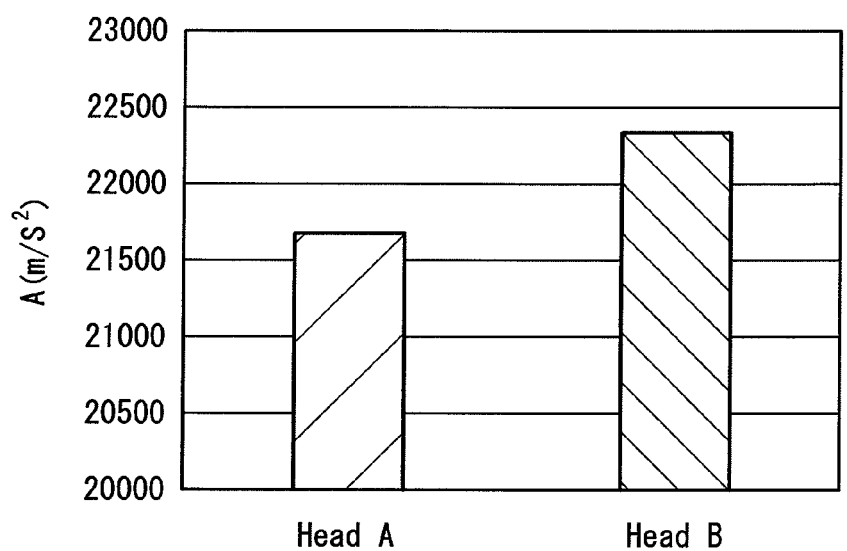

A mean value of the amounts of changes of the acceleration was determined, similarly to the Test 6-1, except that the head speed of the swing was set to 31 m/sec. FIG. 18(b) shows the mean value.

[Test 6-3]

The head A was removed from the shaft and the head B was attached. Then, a positional relation of the shaft and the swing robot remained unchanged. A mean value of the amounts of changes of the acceleration was determined, similarly to the Test 6-1, except that the head B replaced the head A. FIG. 18(a) shows the mean value.

[Test 6-4]

A mean value of the amounts of changes of the acceleration was determined, similarly to the Test 6-2, except that the head B replaced the head A. FIG. 18(b) shows the mean value.

For the result of the sensuous evaluations in FIG. 17(a) and FIG. 17(b) and the evaluation results of FIG. 18(a) and FIG. 18(b), the evaluation results of a same tendency have been obtained. The evaluation method of the present invention has enabled a qualitative evaluation which is closer to a sensuous evaluation and shows small fluctuations.

The methods described above may be applied to an evaluation of hit feeling of sport implements, such as every sport hitting tool and a ball.

The above description is only an example and various changes may be added in a scope that does not depart from the essence of the invention.

What is claimed is:

1. An evaluation method for hit feeling of a sport implement, comprising:
an acceleration measurement step for measuring an acceleration of a sport hitting tool by a sensor; and
a data analysis step for analyzing data obtained in the acceleration measurement step by an information processor,
wherein the data analysis step further comprises the steps of:
determining a first cycle of acceleration of vibration of the sport hitting tool after hitting on the basis of the acceleration of the sport hitting tool, wherein the first cycle is a cycle from the hit time, where the acceleration of vibration is zero, through a period in which the acceleration of vibration after hitting returns to zero after the acceleration of vibration swings to either a minus direction or a plus direction with respect to a time axis, and then returns to zero after the acceleration of vibration further swings to the other direction;
calculating an amount of change in the acceleration in the first cycle of the acceleration of vibration after hitting; and
evaluating the hit feeling based on a magnitude of the amount of change in the acceleration,
wherein in the data analysis step, a predetermined time is set so that the amount of change in acceleration in the first cycle is determined, and the predetermined time is within 1.5 msec from time of hitting, and is a period of time including a maximum value and a minimum value of the acceleration of the first cycle.

2. The evaluation method according to claim 1, wherein in the data analysis step, a predetermined time is set so that an amount of change in acceleration in the first cycle is determined, the amount of change in the acceleration in the first cycle of predetermined time is calculated, and the predetermined time is equal to or longer 0.3 msec from time of hitting.

3. The evaluation method according to claim 1, wherein the amount of change in the acceleration is calculated by using a difference between maximum acceleration and minimum acceleration in the first cycle of vibration.

4. The evaluation method according to claim 1, wherein in the acceleration measurement step, a swing robot holds the sport hitting tool.

5. The evaluation method according to claim 1, wherein the sport hitting tool comprises a holding section to be held by a person, a hitting section for hitting a ball, and a shaft section connecting the hitting section with the holding section, and
in the acceleration measurement step, a sensor for measuring acceleration is attached to the shaft section at a location that is spaced apart from the hitting section.

6. The evaluation method according to claim 5, wherein a ratio (L1/L) of length L of the shaft section to length L1 from the location where the sensor is attached, to a tip of the holding section, which is connected to the shaft section, is equal to or smaller than 0.75.

7. The evaluation method according to claim 5, wherein a ratio (L1/L) of length L of the shaft section to length L1 from the location where the sensor is attached, to a tip of the holding section, which is connected to the shaft section, is equal to or smaller than 0.50.

8. The evaluation method according to claim 5, wherein a ratio (L1/L) of length L of the shaft section to length L1 from the location where the sensor is attached, to a tip of the holding section, which is connected to the shaft section, is equal to or smaller than 0.25.

9. The evaluation method according to claim 1, wherein the sport hitting tool comprises a holding section to be held by a person, a hitting section for hitting a ball, and a shaft section connecting the hitting section with the holding section, and
the hitting section is detachably attached to the shaft section.

10. The evaluation method according to claim 9, wherein the acceleration measurement step comprises a hitting section preparation step, a hitting section replacement step, and a measurement data acquisition step,
in the hitting section preparation step, multiple hitting sections including a first hitting section and a second hitting section are prepared,
in the hitting section replacement step, the first hitting section is removed from the shaft section, the second hitting section is attached to the shaft section, and the removal of the first hitting section is performed after acceleration is measured with the sport hitting tool provided with the first hitting section, and
in the measurement data acquisition step, acceleration is measured with the sport hitting tool provided with the second hitting section.

11. The evaluation method according to claim 1, wherein the sport hitting tool comprises a holding section to be held by a person, a hitting section for hitting a ball, and a shaft section connecting the hitting section with the holding section, and
the hitting section comprises a casing and a face for hitting the ball, and the face is detachably attached to the casing.

12. The evaluation method according to claim 11, wherein the acceleration measurement step comprises a face preparation step, a face replacement step, and a measurement data acquisition step,
in the face preparation step, multiple faces including a first face and a second face are prepared,
in the face replacement step, the first face is removed from the casing, the second face is attached to the casing, and the removal of the first face is performed after acceleration is measured with the sport hitting tool provided with the first face, and
in the measurement data acquisition step, acceleration is measured with the sport hitting tool provided with the second face.

13. The evaluation method according to claim 1, wherein the sport implement is a golf club or a golf ball.

14. The evaluation method according to claim 13, wherein a loft angle of the golf club is equal to or greater than 20°.

15. The evaluation method according to claim 13, wherein a loft angle of the golf club is equal to or greater than 40°.

16. The evaluation method according to claim 13, wherein a loft angle of a golf club for hitting the golf ball is equal to or greater than 20°.

17. The evaluation method according to claim 13, wherein a loft angle of a golf club for hitting the golf ball is equal to or greater than 40°.

18. The evaluation method according to claim 13, wherein the amount of change in the acceleration is calculated by using an amount of change in acceleration Ax in an X-axis direction which is an axial direction of a shaft section of the sport hitting tool.

19. The evaluation method according to claim 13, wherein the amount of change in the acceleration is calculated by using two or more amounts of change among an amount of change in acceleration Ax in an X-axis direction which is an axial direction of a shaft section of the sport hitting tool, an amount of change in acceleration Az in a Z-axis direction which is perpendicular to the X-axis direction and parallel to a hitting direction, and an amount of change in acceleration Ay in a Y-axis direction which is perpendicular to the X-axis direction and the Z-axis direction, and wherein said two or more amounts of change includes at least the amount of change in acceleration Ax in the X-axis direction.

* * * * *